(12) United States Patent
Davis

(10) Patent No.: US 8,227,219 B2
(45) Date of Patent: Jul. 24, 2012

(54) METHOD AND APPARATUS FOR BIO-FUEL SEEDING

(76) Inventor: Tommy Mack Davis, Spartanburg, SC (US)

( * ) Notice: Subject to any disclaimer, the term of this patent is extended or adjusted under 35 U.S.C. 154(b) by 310 days.

(21) Appl. No.: 12/462,086

(22) Filed: Jul. 29, 2009

(65) Prior Publication Data

US 2010/0047888 A1    Feb. 25, 2010

Related U.S. Application Data

(60) Provisional application No. 61/137,254, filed on Jul. 29, 2008.

(51) Int. Cl.
*C12P 7/06* (2006.01)
(52) U.S. Cl. ........................................ 435/161
(58) Field of Classification Search .................. 435/161
See application file for complete search history.

(56) References Cited

U.S. PATENT DOCUMENTS

| 4,775,650 | A | * | 10/1988 | Portier | ........................... 502/62 |
| 4,859,594 | A | * | 8/1989 | Portier | .......................... 435/448 |
| 5,534,143 | A | * | 7/1996 | Portier et al. | .................. 210/151 |

* cited by examiner

*Primary Examiner* — Herbert J Lilling
(74) *Attorney, Agent, or Firm* — Ted M. Anthony

(57) ABSTRACT

A method and apparatus is provided for microbial seeding and amendment of traditional alternative fuels production systems and processes using immobilized microbe bioreactors. The system addition utilizes attachment of yeast or other microbial consortia to a substrate to enhance alternative fuels production in fermentation processes. The system allows for the maintenance of a constant concentrated microbial population, thus enhancing alternative fuels production by stabilizing microbial populations. Desired aerobic and anaerobic conditions are maintained using a microbubble aeration device coupled to the Immobilized Microbe Bioreactor (IMBR) seeding reactors. Generation of the microbial populations for seeding requires control of aerobic and anaerobic conditions to ensure growth of a microbial population acclimated to elevated alternative fuels concentrations.

1 Claim, 3 Drawing Sheets

METHOD AND APPARATUS FOR BIO-FUEL SEEDING

CROSS REFERENCES TO RELATED APPLICATION

Priority of U.S. provisional patent application Ser. No. 61/137,254 filed Jul. 29, 2008, Incorporated Herein by Reference, is Hereby Claimed.

STATEMENTS AS TO THE RIGHTS TO THE INVENTION MADE UNDER FEDERALLY SPONSORED RESEARCH AND DEVELOPMENT

None

BACKGROUND OF THE INVENTION

1. Field of the Invention

The present invention pertains to a method and apparatus for the production of bio-fuels and related compounds including, but not limited to, ethanol. More particularly, the present invention pertains to a microbial seeding system that can be used in the production of bio-fuels, either as a stand-alone process or as part of an existing fermentation system.

2. Brief Description of the Prior Art

As demand for fossil fuel increases, and supply decreases, the costs associated with such fossil fuels can be significant. Additionally, many believe that consumption of fossil fuels negatively impacts the environment by contributing to global warming. Thus, an effort has been underway to find alternative energy sources that can act as a replacement for conventional fossil fuels.

Much attention has focused on bio-fuels as a possible alternative to fossil fuels. Generally, bio-fuels are solid, liquid or gaseous fuels obtained from relatively recently lifeless or living biological material. By contrast, fossil fuels are derived from long-dead biological material. One such bio-fuel that has received a great deal of attention is ethanol, a primarily plant-based fuel which can be produced from organic sources such as sugar cane, corn, waste paper. Ethanol can also be produced from grains like wheat or sorghum.

Ethanol, also known as ethyl alcohol, is a volatile, flammable, colorless liquid having a wide variety of uses including, but not limited to, as a fuel. For example, ethanol has a long history as a fuel for heat and light, and also as a fuel and/or fuel additive for internal combustion engines. When added to gasoline, ethanol reduces volatile organic compound and hydrocarbon emissions, carcinogenic benzene and butadiene emissions, and particulate matter emissions from internal combustion engines. Ethanol is also widely used as a solvent of substances intended for human contact or consumption. In chemistry, ethanol is both an essential solvent and a feedstock for the synthesis of other products, as well as a fuel to power direct-ethanol fuel cells (DEFC) in order to produce electricity.

Although ethanol can be produced via the hydration of ethylene, it is commonly produced biologically through the process of culturing yeast under certain desired conditions (this process is commonly referred to as fermentation). When certain species of yeast (for example, *Saccharomyces cerevisiae*) metabolize sugar, the yeast can produce ethanol and carbon dioxide. Ethanol can also be produced biologically from starchy materials such as cereal grains; however, in such cases, the starchy material must first be converted into sugar(s).

Feed stocks for the production of ethanol can include, but are not limited to, sugarcane juice, sugarcane syrup, molasses, bagasse, corn, fruit juice and concentrates, purified sugars such as sucrose, glucose, fructose, maltose, and syrup mixtures containing simple sugars such as those found in drink syrups.

Existing processes for the production of ethanol have proven to be inefficient and expensive, and frequently require a large amount of space. Thus, there is a need for a seeding process that can be used to improve overall efficiency, while reducing costs and space requirements, associated with conventional ethanol production processes.

SUMMARY OF THE PRESENT INVENTION

In the preferred embodiment, the seeding system of the present invention generally comprises:
- at least one pre-fermentation nutrient amendment/antibiotic tank and pump;
- make-up water supply lines for feedstock concentration control;
- at least one pre-fermentation mixing/holding tank;
- at least one immobilized microbe bioreactor ("IMBR"); and
- at least one surge tank for consistent flow of seeding material to secondary fermentation tanks.

In the preferred embodiment, the present invention beneficially comprises at least one IMBR cluster having a plurality of IMBR microbial generation reactors, beneficially including oxygen source(s) for periodic oxygenation of such generation reactors. Such oxygen can be introduced as air pumped via conventional fans or air blowers, or as pure oxygen. It is to be observed that the seeding system of the present invention can function as a stand-alone system, or can be incorporated within a traditional fermentation process and system.

In the preferred embodiment, microbial generation and seeding is accomplished using IMBR technology in which microbes are immobilized on a desired substrate. Such IMBR technology beneficially utilizes at least one bio-carrier medium inoculated with desired microbes; said at least one bio-carrier medium can include, without limitation, porous diatomaceous earth solids (such as described in U.S. Pat. No. 4,859,594 and U.S. Pat. No. 4,775,650, which are incorporated herein by reference). In the preferred embodiment, said at least one bio-carrier medium is beneficially coated with a thin film of chitin or other substance, and yeast cells or other beneficial microbes are immobilized on the surfaces of such at least one bio-carrier medium. Further, in the preferred embodiment, at least one micro bubble generator (MBG) immobilized cell reactor (for example, the MBG more fully disclosed in U.S. Pat. No. 5,534,143, which is incorporated herein by reference) is provided for periodic aeration and nutrient addition to a liquid column with bottom-up flow.

By promoting in-situ growth of desired yeast and/or other microbial populations, the present invention promotes microbial growth and acclimation within the fermentation tanks, piping and associated elements of the present invention. Over time, the microbial growth provided by the present invention can result in the spread of yeast and/or other beneficial microbial agents throughout the system, thereby improving the fermentation process and overall system efficiency.

Varying feed stocks can be used for fermentation including, but not limited to, sugars from cellulose and other materials, sugarcane juice, sugarcane syrup, molasses, fruit juice and concentrates, purified sugars such as sucrose, glucose, fructose, maltose, and syrup mixtures containing simple sugars such as those found in drinks syrups.

In the preferred embodiment, such feed stocks are beneficially tested for initial concentrations. Feed stocks falling within desired ranges (such as, for example, between 15 and 30 degrees BRIX [°Bx]) can be directly introduced with nutrient amendment into the seeding system. Feed stocks having higher concentrations can be diluted to meet desired specifications.

In the preferred embodiment, feed streams can be maintained for 8-10 hours. Make up water is provided from clean or recycled sources within the distillation component of the production system. Makeup water, nutrients (such as nitrogen, sulfur, and/or phosphorus containing compounds) and/or antibiotics can be added to the feed stream prior to reactor injection. The pre-fermentation tanks utilize mixing to ensure a homogeneous feed for reactor injection.

Amended feed stocks enter the bottom of the microbial generation reactor. In the preferred embodiment, injection of oxygen from air or other oxygen source using a MBG is computer controlled allowing for oxygenation of the reaction for variable times—generally 45 minutes or less in every 6 or more hours of microbial growth. For the remainder of the generation cycle the reactor is maintained under anaerobic conditions. The oxygenation step of the run cycle allows for enhanced growth of microbial cells and removal of built up residual materials within the reactor.

Flow rates through the reactors can be adjusted based upon seeding volume desired. Reactor sizes can be varied and the void volume within the reactors either filled or partially filled with inoculated media. Reactor size for seeding systems typically depends on the capacity of the alternative fuels plant. Off gases are recaptured using a vacuum system which then returns gases to the MBG.

Data Set 1

These data were produced using an immobilized yeast culture of *Saccharomyces cerevisiae*. Cell growth in preliminary tests indicated 10 9 cells/g biocarrier was achievable in a 3% ethanol broth. Main sugar source within broth was either purified sucrose and micro nutrients or molasses and micronutrients. Data sets reflect ethanol yield of 17-20% without affecting yeast production, immobilization, or feedback inhibition.

Table 1 and FIG. 2 reflect acceptable biomass production using the IMBR system as a seeding device for conventional submerged tank fermentation. Two bench scale IMBR reactors with an 1800 ml void volume were run in series, that is the entire flow passed into the first reactor and then into the second reactor, before the material was deposited into a submerged fermentation tank for final polishing. Aeration periodically was provided by a low flow air source on a timer to allow for appropriate oxygenation to promote cellular growth.

Samples were taken from feed to monitor initial Total Reducing Sugars in fermented medium (TRSf) and after fermentation to determine residual sugar content. A refractometer was used to read initial and final sugar content. Ethanol production was determined via mass distillation and recovery.

As the micro-column population acclimated to the presence of ethanol, the overall alcohol content/production increased until a maximum production of ~20 g/L was detected at 72 hours continuous flow and feeding.

TABLE 1

Submerged Tank Fermentation: IMBR system as seeding system

| Time (hours) | Initial Control TRSf (g/L) | Residual TRSf (g/L) | Ethanol Yield (g/L) |
|---|---|---|---|
| 0 | 160 | 160 | |
| 3 | 162 | 144 | |
| 6 | 158 | 151 | |
| 9 | 161 | 133 | 11 |
| 12 | 160 | 144 | 12 |
| 15 | 157 | 151 | 12 |
| 22 | 162 | 98 | 13 |
| 28 | 158 | 97 | 18 |
| 32 | 155 | 91 | 18 |
| 39 | 159 | 89 | 19 |
| 42 | 157 | 88 | 19 |
| 48 | 158 | 84 | 19 |
| 52 | 156 | 78 | 21 |
| 60 | 160 | 71 | 20 |
| 72 | 160 | 69 | 21 |

Data Set 2

Using the IMBR reactor in a parallel recycle mode similar to conventional submerged tank fermentation improved ethanol yields from 21 g/L to 41 g/L for a feed of 160±12 g/L TRSf. (see Table 2/FIG. 3). The reactors were fed in parallel rather than in series with a portion of the primary fermentation tank volume recycled to the IMBRs for further polishing. The primary fermentation tank provided only minimal addition to ethanol content as produced from direct contact with IMBR columns.

TABLE 2

Parallel Feed Fermentation using an IMBR system with tanks

| Time (hours) | Feed TRSf (g/L) | Export TRSf (g/L) | Ethanol Yield (g/L) |
|---|---|---|---|
| 0 | 160 | 160 | |
| 3 | 162 | 108 | |
| 6 | 158 | 101 | |
| 9 | 161 | 98 | 12 |
| 12 | 157 | 95 | 15 |
| 15 | 157 | 89 | 28 |
| 22 | 162 | 84 | 32 |
| 28 | 158 | 88 | 38 |
| 32 | 155 | 78 | 45 |
| 39 | 159 | 75 | 41 |
| 42 | 157 | 72 | 41 |
| 48 | 158 | 77 | 42 |
| 52 | 156 | 58 | 42 |
| 60 | 158 | 58 | 38 |
| 72 | 154 | 49 | 39 |
| 96 | 151 | 55 | 38 |
| 110 | 162 | 59 | 32 |
| 120 | 161 | 34 | 35 |
| 140 | 158 | 35 | 34 |

Thus, it is an object of the present invention to provide a process for permanent immobilization of microbes (such as yeast, *Saccharomyces cerevisiae*, or bacterial consortia having one or more beneficial organisms) on a substrate for the purpose of enhancing fermentation of carbohydrate based feed stocks to produce bio-fuels and/or other alternative fuels including, but not limited to, ethanol, butanol, methanol, biodiesel and others. Such process beneficially increases the population of such organisms allowing for highly concentrated and consistent populations for fermentation in a traditional fermentation system, while allowing for maintenance of a pure culture suppressing infection by other microbial species within the fermentation system.

It is a further object of the present invention to reduce the time for fermentation of stock material to alternative fuel source as compared to traditional fermentation systems, as well as a reduction in the size of the subject fermentation system.

It is a further object of the present invention to utilize an ultra efficient aeration system, such as one or more immobilized microbe bioreactors, to enhance growth and stability of microbial populations through cycling of aerobic and anaerobic conditions during selected time periods. The flow through an IMBR cluster can be tailored to accommodate feed stocks so that each IMBR within a cluster can run in parallel, or in series, as desired.

It is a further object of the present invention to beneficially cycle aerobic and anaerobic conditions to enhance microbe growth, as well as population acclimation, to increasing alternative fuel material concentrations as found under fermentation conditions.

The seeding system of the present invention, when using food grade materials and control, is appropriate for the generation of microbes for use in food related fermentation such as the production of beer, wine, cheese, yogurt, and other fermented food products. Likewise, the seeding system of the present invention, when using medical grade materials and control, is appropriate for the generation of medical related microbes and the materials they manipulate or generate.

BRIEF DESCRIPTION OF THE DRAWINGS

The foregoing summary, as well as the following detailed description of the preferred embodiments, is better understood when read in conjunction with the appended drawings. For the purpose of illustrating the invention, the drawings show certain preferred embodiments. It is understood, however, that the invention is not limited to the specific methods and devices disclosed.

DETAILED DESCRIPTION OF A PREFERRED EMBODIMENT OF THE INVENTION

Figure 1:
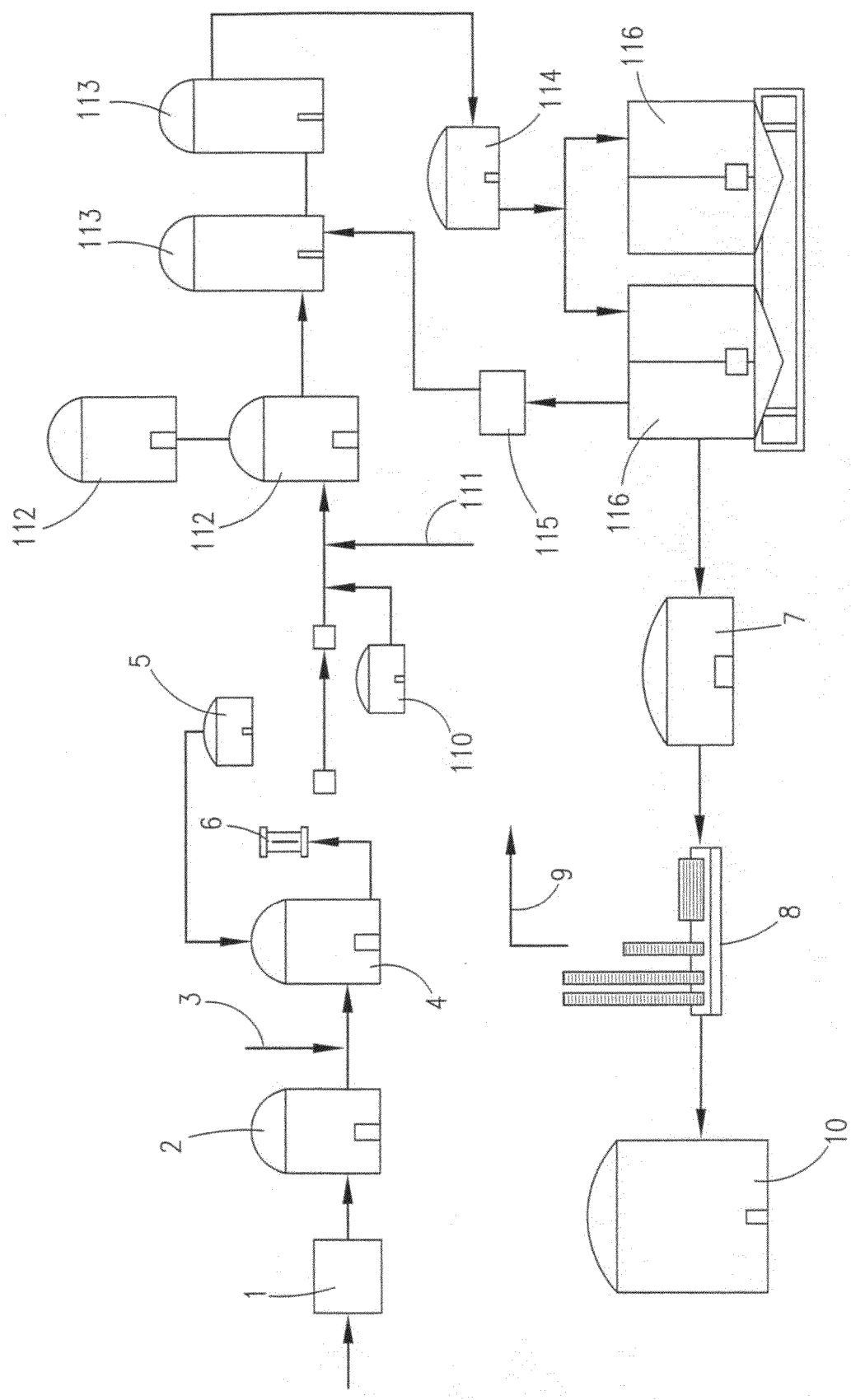
FIG. 1 depicts a schematic layout of the seeding system of the present invention incorporated within a conventional ethanol production system.
Figure 2:
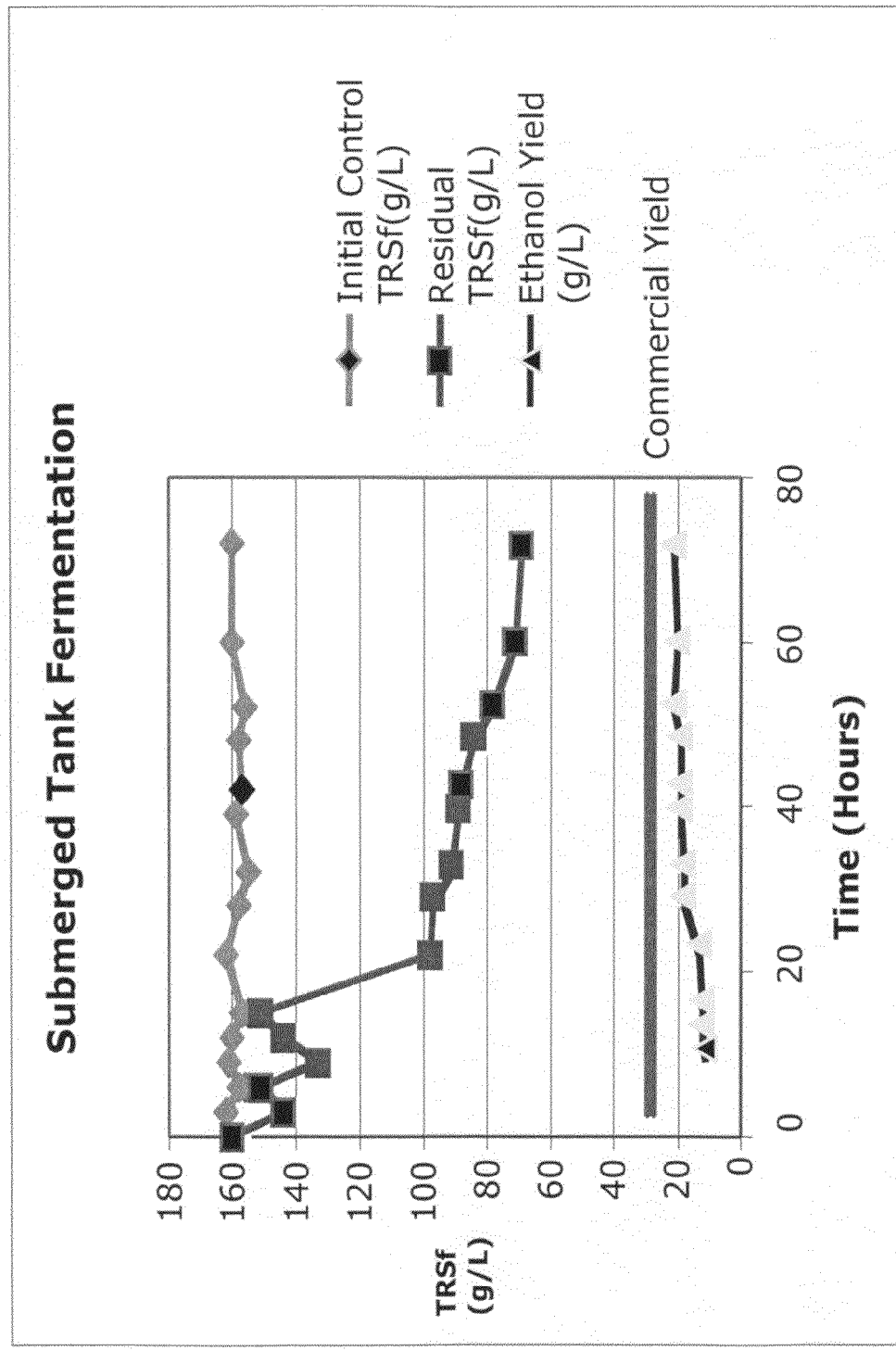
FIG. 2 depicts a graphical representation of the data set displayed in Table 1.
Figure 3:
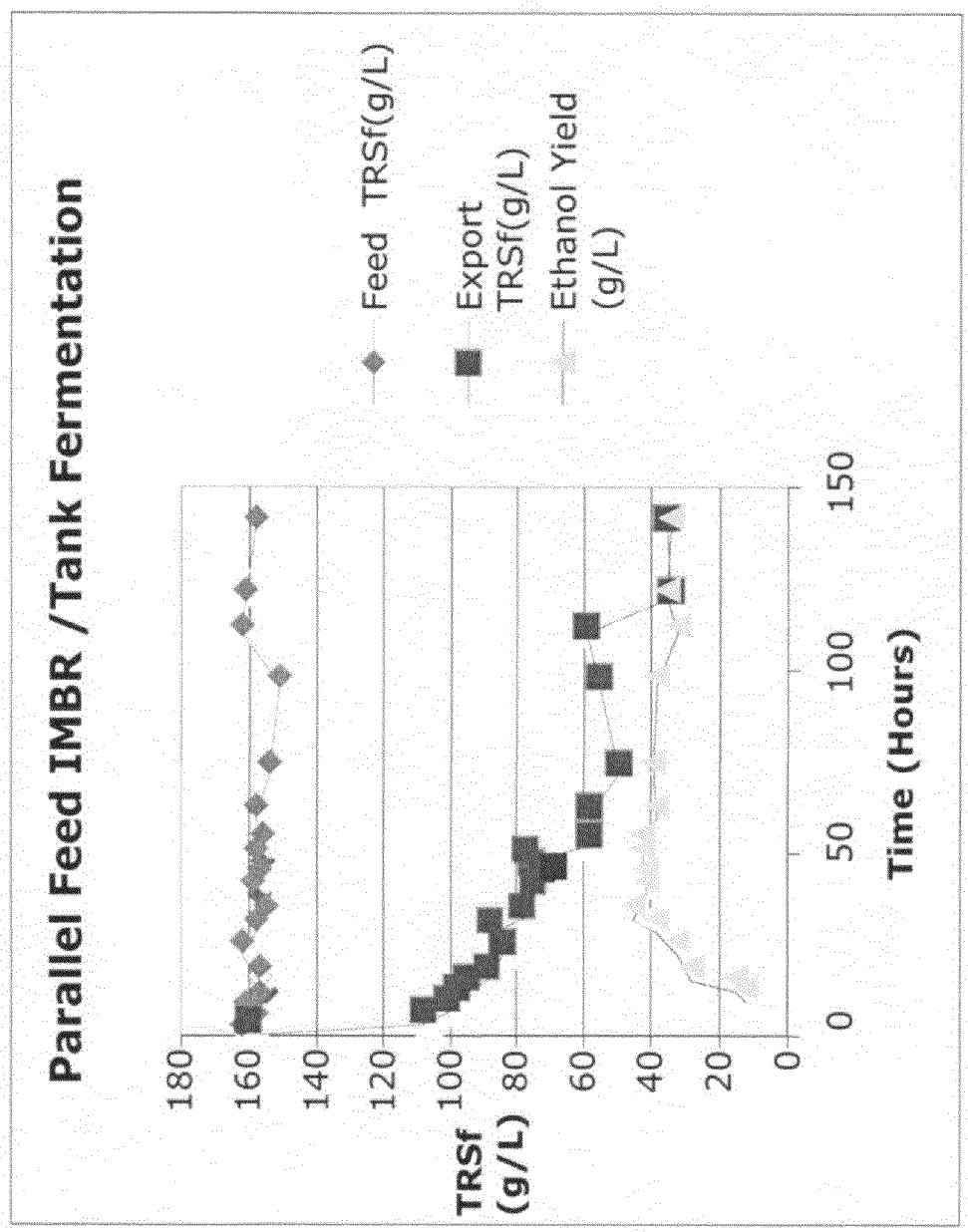
FIG. 3 depicts a graphical representation of the data set displayed in Table 2.

FIG. 1 depicts a schematic layout of the seeding system of the present invention incorporated within a conventional ethanol production system. It is to be observed that the seeding system of the present invention can function as a stand-alone system, or can be incorporated within a traditional fermentation process and system.

For illustration purposes, such conventional ethanol production system comprises various components for treatment of feed stocks, including hammer mill 1, slurry tank 2, steam input line 3, and liquefaction tank 4. Additionally, optional additive supply tank 5 (for enzymes or other desired additives) and mash cooking component 6 can be provided. It is to be observed that the aforementioned components of conventional ethanol production system are generally well known in the art; Further, the selection of such components is generally dictated by the type and quality of feed stock utilized, and may be varied (with certain components being added or deleted) depending upon a particular application.

In the preferred embodiment, the seeding system of the present invention generally comprises at least one pre-fermentation nutrient amendment/antibiotic tank 110 (and associated pump, not shown in FIG. 1); make-up water line(s) 111 for feed stock concentration control; at least one pre-fermentation mixing/holding tank 112 to ensure homogeneity of feed prior to reactor injection; at least one immobilized microbe bioreactor ("IMBR") microbial generation reactor 113; and at least one surge tank 114 for consistent flow of seeding material to secondary fermentation tanks.

In most cases, the present invention beneficially includes a plurality of IMBR microbial generation reactors 113 arranged in a cluster. Such IMBR microbial generation reactors 113 further include at least one oxygen source (not depicted in FIG. 1) for periodic oxygenation of such IMBR microbial generation reactors 113. Oxygen can be introduced as air pumped via conventional fans or air blowers, or as pure oxygen.

In the preferred embodiment, microbial generation and seeding is accomplished using IMBR technology. As set forth above, such IMBR technology beneficially utilizes at least one bio-carrier medium inoculated with desired microbes; said at least one bio-carrier medium can include, without limitation, porous diatomaceous earth solids (such as described in U.S. Pat. No. 4,859,594 and U.S. Pat. No. 4,775,650, which are incorporated herein by reference). In the preferred embodiment, said at least one bio-carrier medium is beneficially coated with a thin film of chitin or other substance. Yeast cells or other beneficial microbes are immobilized on the surfaces of such at least one bio-carrier medium. Further, in the preferred embodiment, at least one micro bubble generator (MBG) immobilized cell reactor (for example, the MBG more fully disclosed in U.S. Pat. No. 5,534,143, which is incorporated herein by reference) is provided for periodic aeration and nutrient addition to a liquid column with bottom-up flow.

By promoting in-situ growth of desired yeast and/or other microbial populations, the present invention promotes microbial growth and acclimation within the fermentation tanks, piping and associated elements of the present invention. Over time, the microbial growth provided by the present invention can result in the spread of yeast and/or other beneficial microbial agents throughout the system, thereby improving the fermentation process and overall system efficiency.

In operation, the seeding system of the present invention is utilized in connection with conventional ethanol fermentation system depicted in FIG. 1. At least one feed stock is supplied at the inlet of said conventional fermentation system (which, in FIG. 1, is depicted as hammer mill 1). Varying feed stocks can be used for fermentation including, but not limited to, sugars from cellulose and other materials, sugarcane juice, sugarcane syrup, bagasse, corn, molasses, fruit juice and concentrates, purified sugars such as sucrose, glucose, fructose, maltose, and syrup mixtures containing simple sugars such as those found in drinks syrups.

In the preferred embodiment, such feed stocks are beneficially tested for initial concentrations. Feed stocks falling within desired ranges [such as, for example, between 15 and 30 degrees BRIX (°Bx)] can be directly introduced with nutrient amendment (from at least one pre-fermentation nutrient amendment/antibiotic tank 110) into the seeding system of the present invention. Feed stocks having higher concentrations can be diluted to meet desired specifications using water source line(s) 111.

In the preferred embodiment, make up water is provided from clean or recycled sources via water line(s) 111 within the distillation component of the production system. Makeup water, nutrients (such as nitrogen, sulfur, and/or phosphorus containing compounds) and/or antibiotics can be added to the feed stream prior to reactor injection via at least one pre-fermentation nutrient amendment/antibiotic tank 110. Mixing can be provided in pre-fermentation tank(s) 112 to ensure a homogeneous feed for reactor injection.

High quality feed stock is collected in holding tanks (volume) prior to amendment and held for no more than 8-12 hours before nutrient and antibiotic addition to the stream. In the preferred embodiment, mixing is continuous in both the holding tanks and the pre-fermentation mixing tanks during microbial generation to maintain desired BRIX value (usually 10 or higher). BRIX values of the feed stock to the main fermentation plant may also be used as a seeding influent. Automatic sampling and testing of feed stock concentration is beneficially used to monitor concentration and determine makeup water volume to be added in the mixing tank. In the preferred embodiment, nutrient addition occurs as needed based upon observed BRIX values. Antibiotics can also be added based upon feed concentration.

In the preferred embodiment of the present invention, amended feed stocks enter the bottom of IMBR microbial generation reactors 113. Injection of oxygen from air or other oxygen source using a Micro bubble Generator (MBG) is beneficially computer controlled, allowing for oxygenation of the reaction for variable times. Although it is subject to adjustment, such times will generally be 45 minutes or less in every 6 or more hours of microbial growth. For the remainder of each generation cycle, the reactor can be beneficially maintained under anaerobic conditions. The oxygenation step of the run cycle allows for enhanced growth of microbial cells and removal of built up residual materials within the reactor.

An electronically monitored and controlled aeration protocol may be used to maintain appropriate oxygenation to speed microbial growth without loss of total alternative fuels production and microbial acclimation. Oxygen sensors can be used to detect oxygen levels within reactor outflow during the aeration cycle.

Flow rates through the reactors can be tailored based upon seeding volume desired. Reactor sizes can be varied and the void volume within the reactors either filled or partially filled with inoculated media. Reactor size for seeding systems depends on the capacity of the alternative fuels plant. In the preferred embodiment, off gases (including, without limitation, CO2) can be recaptured using a vacuum system 115 and returned to the MBG. In the preferred embodiment, split flow supplies feed material to microbial generation reactors 113, typically arranged in a cluster, and main fermentation tanks 116 (having an outlet for the removal of settled solids) at a rate depending upon the capacity of the plant.

For generation of microbes, reactors can be fed in series where a first reactor receives standardized amended feed, which is thereafter sent to reactor 2 via a surge tank. Alternatively, both reactors can receive separate constant feed for generation of microbes to be collected in a surge tank for continuous feed to the primary fermentation step. A high flow rate will ensure maintenance of the exponential growth stage in microbial lifecycles, and partial generation of alternative fuels will maintain a culture acclimated to increased alternative fuels concentrations.

Microbial concentration can be monitored daily to ensure constant and concentrated seeding to the primary fermentation tank. Samples can be pulled from multiple locations within the reactors.

Although the specific components of conventional ethanol production system may vary, FIG. 1 depicts out flow from main fermentation tanks 116 piped to pre-distillation surge tank 7. Fluids from such pre-distillation surge tank can then be directed to distillation plant 8, having recovered water line 9. In the preferred embodiment, recovered water line 9 is in fluid communication with make-up water line 111. Following distillation, ethanol product can be directed to storage tank 10 for subsequent handling.

The above-described invention has a number of particular features that should preferably be employed in combination, although each is useful separately without departure from the scope of the invention. While the preferred embodiment of the present invention is shown and described herein, it will be understood that the invention may be embodied otherwise than herein specifically illustrated or described, and that certain changes in form and arrangement of parts and the specific manner of practicing the invention may be made within the underlying idea or principles of the invention.

What is claimed:
1. A method of producing ethanol comprising:
   a. supplying feed stock into a first container, wherein said feed stock contains at least one type of sugar;
   b. measuring the sugar concentration of said feed stock;
   c. adjusting said sugar concentration of said feed stock to fall within a predetermined range;
   d. introducing said feed stock from said first container into a bio-reactor, wherein said bio-reactor comprises:
      (i) a second container;
      (ii) at least one substrate disposed within said second container,
   wherein said at least one substrate is inoculated with at least one microbial population, preselected for fermentation capability, and said at least one microbial population propagates on the surface of said at least one substrate;
   e. supplying oxygen to said bio-reactor and said at least one microbial population; and
   f. fermenting said feed stock within said bio-reactor to generate ethanol.

* * * * *